United States Patent
Becker et al.

(10) Patent No.: US 9,663,418 B2
(45) Date of Patent: May 30, 2017

(54) SYSTEM AND PROCESS FOR MAKING CYCLOHEXYLBENZENE

(71) Applicant: ExxonMobil Chemical Patents Inc., Baytown, TX (US)

(72) Inventors: Christopher L. Becker, Manhattan, KS (US); James R. Lattner, LaPorte, TX (US); Francisco M. Benitez, Cypress, TX (US); Charles Morris Smith, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 1 day.

(21) Appl. No.: 14/763,736

(22) PCT Filed: Feb. 21, 2014

(86) PCT No.: PCT/US2014/017733
§ 371 (c)(1),
(2) Date: Jul. 27, 2015

(87) PCT Pub. No.: WO2014/137628
PCT Pub. Date: Sep. 12, 2014

(65) Prior Publication Data
US 2015/0361009 A1    Dec. 17, 2015

Related U.S. Application Data

(60) Provisional application No. 61/772,462, filed on Mar. 4, 2013.

(30) Foreign Application Priority Data

May 7, 2013  (EP) .................................. 13166822

(51) Int. Cl.
*B01J 8/00*    (2006.01)
*B01J 8/02*    (2006.01)
(Continued)

(52) U.S. Cl.
CPC ................ *C07C 2/74* (2013.01); *B01D 3/143* (2013.01); *B01J 8/0214* (2013.01); *B01J 19/245* (2013.01);
(Continued)

(58) Field of Classification Search
CPC .... C07C 2/00; C07C 2/54; C07C 2/72; C07C 2/74; C07C 5/00; C07C 5/32;
(Continued)

(56) References Cited

U.S. PATENT DOCUMENTS 3,864,421 A * 2/1975 Suggitt ..................... C07C 2/74
585/263
4,230,638 A    10/1980 Murtha
(Continued)

FOREIGN PATENT DOCUMENTS

CN    102448915 A    5/2012
CN    203976670 U    12/2014
(Continued)

*Primary Examiner* — Natasha Young

(57) ABSTRACT

A system for making cyclohexylbenzene starting from benzene and hydrogen includes a first benzene preparation column, a hydroalkylation reactor, a dehydrogenation reactor, a second distillation column for cyclohexylbenzene separation, a third distillation column for cyclohexylbenzene purification, a transalkylation reactor, and a fourth distillation column for separating cyclohexylbenzene from transalkylation effluent. All components are integrated to achieve a high-purity cyclohexylbenzene product produced with a high yield and high overall energy efficiency.

24 Claims, 1 Drawing Sheet

(51) Int. Cl.
  *B01J 19/00* (2006.01)
  *B01J 19/24* (2006.01)
  *C07C 2/72* (2006.01)
  *C07C 2/74* (2006.01)
  *C07C 5/32* (2006.01)
  *C07C 5/367* (2006.01)
  *C07C 6/06* (2006.01)
  *C07C 13/28* (2006.01)
  *B01D 3/00* (2006.01)
  *B01D 3/14* (2006.01)
  *C07C 2/00* (2006.01)
  *C07C 2/54* (2006.01)
  *C07C 5/00* (2006.01)
  *C07C 6/00* (2006.01)
  *C07C 6/02* (2006.01)
  *C07C 6/04* (2006.01)
  *C07C 13/00* (2006.01)

(52) U.S. Cl.
  CPC ............... *C07C 5/367* (2013.01); *C07C 6/06* (2013.01); *B01J 2208/027* (2013.01); *B01J 2219/0004* (2013.01); *B01J 2219/00006* (2013.01); *B01J 2219/00103* (2013.01); *B01J 2219/24* (2013.01); *C07C 2101/14* (2013.01); *C07C 2523/40* (2013.01)

(58) Field of Classification Search
  CPC .. C07C 5/367; C07C 6/00–6/06; C07C 13/00; C07C 13/28; C07C 2101/00; C07C 2101/12; C07C 2101/14; C07C 2523/00; C07C 2523/38; C07C 2523/40; B01D 3/00; B01D 3/14; B01D 3/141; B01D 3/143; B01J 8/00; B01J 8/02; B01J 8/0207; B01J 8/0214; B01J 19/00; B01J 19/24; B01J 19/245; B01J 2208/02; B01J 2208/023; B01J 2208/027; B01J 2219/00002–2219/00006; B01J 2219/00027; B01J 2219/0004; B01J 2219/00049; B01J 2219/00051; B01J 2219/00074; B01J 2219/00087; B01J 2219/00103

See application file for complete search history.

(56) References Cited

U.S. PATENT DOCUMENTS

| | | |
|---|---|---|
| 4,306,944 A | 12/1981 | Murthy et al. |
| 6,037,513 A | 3/2000 | Chang et al. |
| 6,049,018 A | 4/2000 | Calabro et al. |
| 6,720,462 B2 | 4/2004 | Kuhnle et al. |
| 6,730,625 B1 | 5/2004 | Chang et al. |
| 7,579,511 B1 | 8/2009 | Dakka et al. |
| 8,633,343 B2 | 1/2014 | Wang et al. |
| 9,321,711 B2 | 4/2016 | Becker et al. |
| 2014/0371498 A1* | 12/2014 | Kuechler ............... C07C 2/74 585/252 |
| 2015/0361009 A1 | 12/2015 | Becker et al. |
| 2015/0375135 A1 | 12/2015 | Becker et al. |

FOREIGN PATENT DOCUMENTS

| | | |
|---|---|---|
| GB | 929680 | 6/1963 |
| WO | 2009/128984 | 10/2009 |
| WO | 2009/131769 | 10/2009 |
| WO | 2011/001244 | 1/2011 |
| WO | 2011/100013 | 8/2011 |
| WO | 2012/036822 | 3/2012 |
| WO | WO 2012/082232 A1 * | 6/2012 |
| WO | 2013/058882 | 4/2013 |
| WO | 2013/165656 | 11/2013 |
| WO | 2013/165659 | 11/2013 |

\* cited by examiner

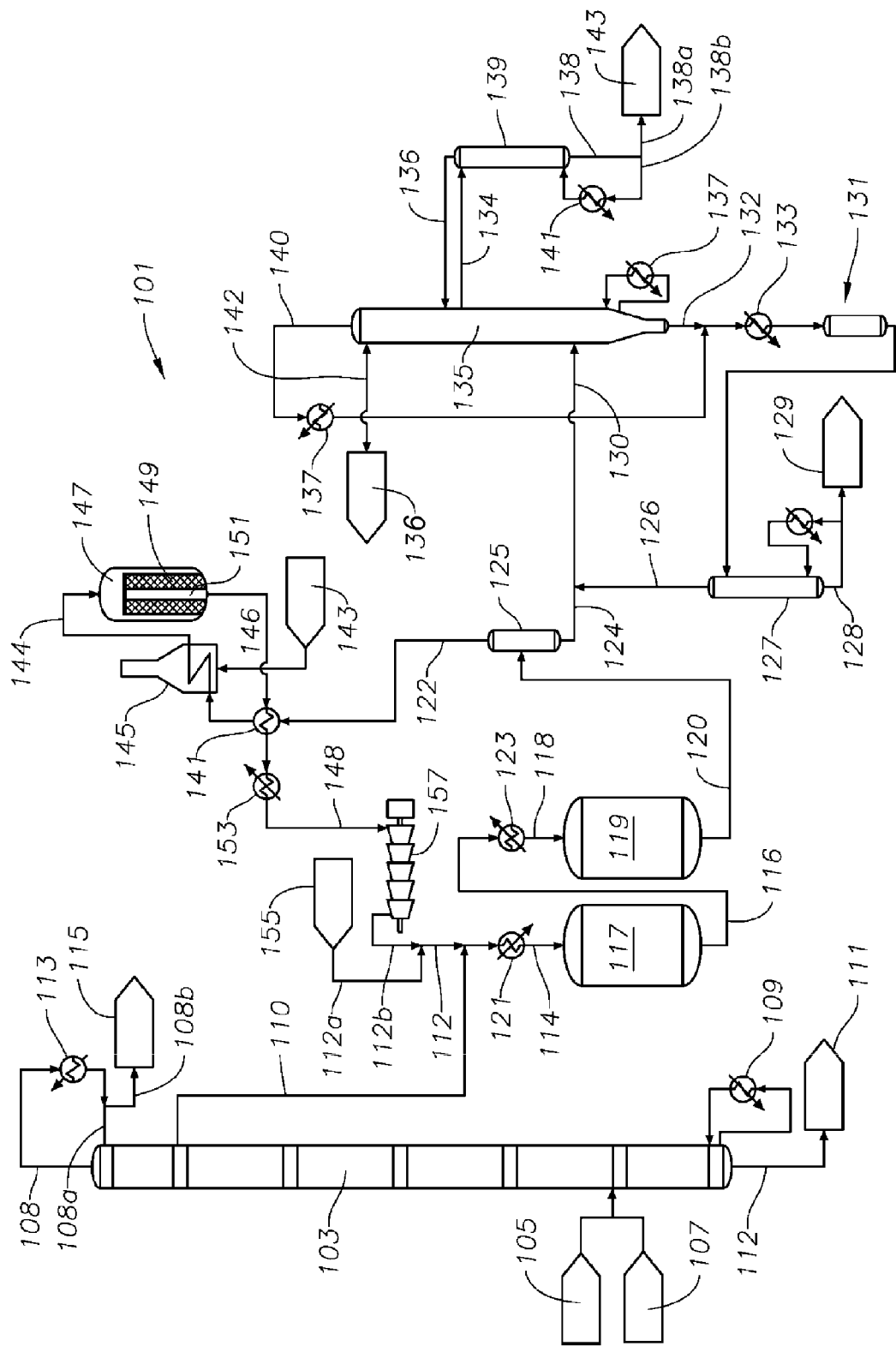

SYSTEM AND PROCESS FOR MAKING CYCLOHEXYLBENZENE

PRIORITY CLAIM TO RELATED APPLICATIONS

This application is a National Stage Application of International Application No. PCT/US2014/017733, now WO2014/137628, filed Feb. 21, 2014, which claims priority to U.S. Provisional Application Ser. No. 61/772,462 filed Mar. 4, 2013, and European Application No. 13166822.0 filed May 7, 2013, the disclosures of which are fully incorporated herein by their reference.

FIELD

The present invention relates to systems and processes for making cyclohexylbenzene. In particular, the present invention relates to systems and processes for making cyclohexylbenzene by benzene hydroalkylation. The present invention is useful, e.g., in making phenol and cyclohexanone starting from benzene hydroalkylation.

BACKGROUND

The production of phenol from cyclohexylbenzene is an emerging technology, interesting in that it co-produces cyclohexanone, rather than acetone. In this process, cyclohexylbenzene is first oxidized to form hydroperoxide thereof, which is then cleaved in the presence of an acid catalyst to obtain phenol and cyclohexanone.

Cyclohexylbenzene may be produced, for example, by direct alkylation of benzene with cyclohexene, or by hydroalkylation of benzene. In the latter process, benzene reacts with hydrogen in the presence of a catalyst such that the benzene undergoes partial hydrogenation to produce a cyclohexene intermediate, which then alkylates part of the benzene starting material. In this regard, U.S. Pat. No. 6,037,513 has disclosed that cyclohexylbenzene selectivity in the hydroalkylation of benzene can be improved by contacting the benzene and hydrogen with a bifunctional catalyst comprising of at least one hydrogenation metal and a molecular sieve of the MCM-22 type. The hydrogenation metal is preferably selected from palladium, ruthenium, nickel, cobalt, and mixtures thereof and the contacting step is conducted at a temperature of about 50° C. to 350° C., a pressure of about 100 kPa to 7000 kPa, a hydrogen to benzene molar ratio of about 0.01 to 100 and a weight hourly space velocity (WHSV) of about 0.01 hr$^{-1}$ to 100 hr$^{-1}$. This reference discloses that the resultant cyclohexylbenzene can then be oxidized to the corresponding hydroperoxide and the peroxide decomposed to the desired phenol and cyclohexanone. Nonetheless, notwithstanding the high selectivity of the hydroalkylation reaction over the MCM-22 molecular sieve-based bifunctional catalyst in the disclosed method, small amounts of cyclohexane and methylcyclopentane are produced in the hydroalkylation effluent.

The overall benzene conversion rates in the hydroalkylation reaction are typically only 40 wt % to 60 wt %. Therefore, recycle of unreacted benzene is desired. Unless removed, impurities including cyclohexane and methylcyclopentane will tend to build up in the recycle benzene stream thereby displacing benzene and increasing the production of undesirable by-products. Thus, a problem facing the commercial application of cyclohexylbenzene as a phenol precursor is removing the cyclohexane in the benzene recycle streams.

In addition, benzene hydroalkylation is known to produce a non-negligible amount of di-cyclohexylbenzenes and tri-cyclohexylbenzenes, which are typically converted to cyclohexylbenzene via transalkylation with benzene to increase the overall cyclohexylbenzene yield of the process.

SUMMARY

Thus, the overall system for producing cyclohexylbenzene from benzene hydroalkylation is very complex. Careful design of each component and the integration of the overall system is required in order to achieve a high yield, high purity and high energy efficiency.

The present disclosure provides an equipment system comprising an integrated benzene preparation column, a hydroalkylation reaction sub-system, a dehydrogenation sub-system, a cyclohexylbenzene distillation and purification sub-system, and a transalkylation sub-system, capable of continuously producing high-purity cyclohexylbenzene at a high yield and an overall high energy efficiency by benzene hydroalkylation. The present disclosure also provides a process for making cyclohexylbenzene using the system.

A first aspect of the present application relates to a system for producing cyclohexylbenzene from benzene and hydrogen, the system comprising:

(A) a first distillation column configured to receive a benzene feed and to produce a first bottom effluent comprising components having higher boiling points than benzene, a first middle effluent consisting essentially of benzene, and a first upper effluent comprising water, hydrogen and other components having lower boiling point than benzene;

(B) a hydroalkylation device configured to produce a hydroalkylation production mixture comprising benzene, cyclohexane and cyclohexylbenzene, the device comprising a first hydroalkylation reactor, a second hydroalkylation reactor connected in series with the first hydroalkylation reactor and a first heat exchanger in between, wherein:

the first hydroalkylation reactor comprises a first hydroalkylation catalyst bed, is in fluid communication with the first distillation column, is configured to receive (i) at least a portion of the first middle effluent and (ii) hydrogen at a location in the vicinity of the top thereof, to allow the reaction medium to travel downwards through the first hydroalkylation catalyst bed, and to produce a first hydroalkylation effluent at a location in the vicinity of the bottom thereof;

the heat exchanger is configured to cool the first hydroalkylation effluent; and the second hydroalkylation reactor comprises a second hydroalkylation catalyst bed, is configured to receive, at a location in the vicinity of the top thereof, the cooled first hydroalkylation effluent supplied from the heat exchanger, allows the reaction medium to travel downwards through the second hydroalkylation catalyst bed, and produces a second hydroalkylation effluent at a location in the vicinity of the bottom thereof;

(C) a first separation drum for separating the hydroalkylation production mixture into a first lower drum effluent comprising benzene, cyclohexane and cyclohexylbenzene, and an first upper drum effluent comprising hydrogen, benzene and cyclohexane;

(D) a second distillation column in fluid communication with the first separation drum configured to receive at least a portion of the first lower drum effluent and to produce (i) a second lower effluent comprising C18 components at a location in the vicinity of the bottom of the second distillation column, (ii) a second middle effluent comprising benzene and cyclohexylbenzene, and (ii) a second upper effluent comprising benzene at a location in the vicinity of the top of the second distillation column;

(E) a third distillation column in fluid communication with the second distillation column configured to receive at least a portion of the second middle effluent and to produce (i) a third lower effluent comprising at least 90 wt % of cyclohexylbenzene, the percentage based on the total weight of the third lower effluent, and (ii) a third upper effluent comprising benzene at a higher concentration than the second middle effluent, at least a portion of the third upper effluent is recycled to the second distillation column at a location above the second middle effluent;

(F) a transalkylation reactor comprising a transalkylation catalyst bed, configured to receive (i) at least a portion of the second lower effluent and benzene, to allow the transalkylation reaction medium travel downwards, and to produce a transalkylation effluent comprising cyclohexylbenzene, benzene and C18;

(G) a fourth distillation column in fluid communication with the transalkylation reactor configured to receive at least a portion of the transalkylation effluent and to produce a fourth lower effluent comprising C18 and a fourth upper effluent comprising at least 50 wt % of benzene and cyclohexylbenzene, the percentage based on the total weight of the fourth upper effluent, the fourth distillation column is in further fluid communication through which at least a portion of the fourth upper effluent is supplied to the second distillation column;

(H) a dehydrogenation reactor comprising a bed of dehydrogenation catalyst in fluid communication with the first separation drum configured to receive at least a portion of the first upper drum effluent and to produce a dehydrogenation effluent comprising benzene, cyclohexane and hydrogen; and (I) a second separation drum in fluid communication with the dehydrogenation reactor configured to receive the dehydrogenation effluent and to produce a second upper drum effluent comprising hydrogen, and a second lower drum effluent comprising benzene, the second separation drum is in further fluid communication with the first distillation column through which at least a portion of the hydrogen in the second upper drum effluent is recycled to the hydroalkylation device.

A second aspect of the present disclosure relates to a process for making cyclohexylbenzene using the system of the first aspect, above.

BRIEF DESCRIPTION OF THE DRAWINGS

FIG. 1 is a schematic diagram showing an exemplary system and process for making cyclohexylbenzene according to the present disclosure.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more, or even all steps, may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are performed in the order listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two, or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the operation "x" produces the absolute value of the number or variable x.

In the present disclosure, a location "in the vicinity of" an end (top or bottom) of a column means a location within a distance of a*Hc from the end (top or bottom) of the column, where Hc is the height of the column from the bottom to the top, and a1≤a≤a2, where a1 and a2 can be, independently, 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, as long as a1<a2. For example, a location in the vicinity of an end of a column can have an absolute distance from the end (top or bottom) of at most D meters, where D can be 5.0, 4.5, 4.0, 3.5, 3.0, 2.5, 2.0, 1.5, 1.0, 0.8, 0.5, 0.4, 0.3, 0.2, 0.1, or 0.

An "upper effluent" as used herein may be at the very top or the side of a vessel such as a fractionation column or a reactor, with or without an additional effluent above it. Preferably, an upper effluent is drawn at a location in the vicinity of the top of the column. Preferably, an upper effluent is drawn at a location above at least one feed. A "lower effluent" as used herein is at a location lower than the upper effluent, which may be at the very bottom or the side of a vessel, and if at the side, with or without additional effluent below it. Preferably, a lower effluent is drawn at a location in the vicinity of the bottom of the column. Preferably, a lower effluent is drawn at a location below at least one feed. As used herein, a "middle effluent" is an effluent between an upper effluent and a lower effluent.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

As used herein, the generic term "dicylcohexylbenzene" ("DiCHB") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, diicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or in combination with the MCM-22 molecular sieves. Desirably, the molecular sieve is selected from (a) MCM-49, (b) MCM-56, and (c) isotypes of MCM-49 and MCM-56, such as ITQ-2.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

(Reaction-1)

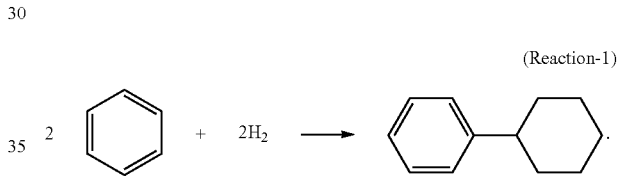

Alternatively, cyclohexylbenzene can be produced by direct alkylation of benzene with cyclohexene in the presence of a solid-acid catalyst such as molecular sieves in the MCM-22 family according to the following Reaction-2:

(Reaction-2)

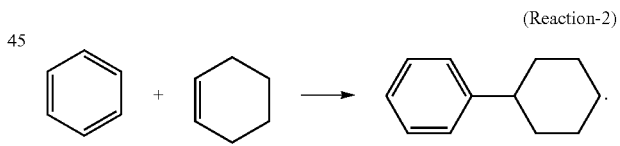

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 $hr^{-1}$ to 10 $hr^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

The cyclohexylbenzene feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

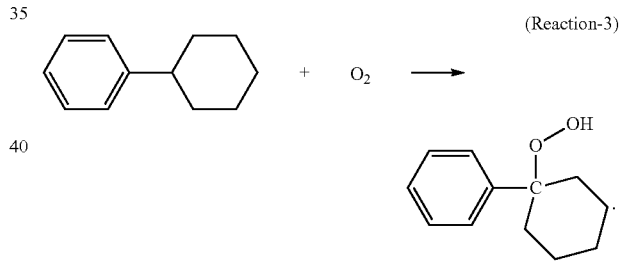

(Reaction-3)

In exemplary processes, the oxidizing step may be accomplished by contacting an oxygen-containing gas, such as air and various derivatives of air, with the feed comprising cyclohexylbenzene. For example, a stream of pure $O_2$, $O_2$ diluted by inert gas such as $N_2$, pure air, or other $O_2$-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

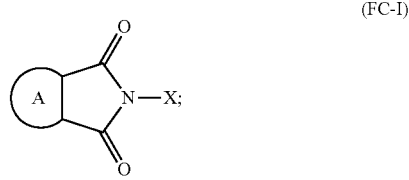

(FC-I)

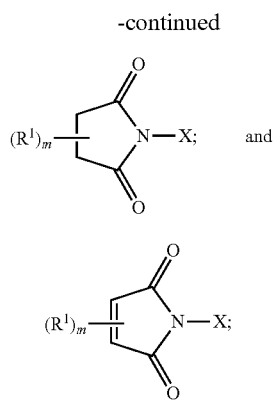

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

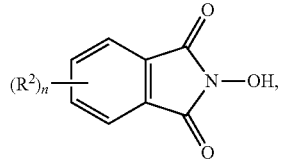

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from Cu1 wt % to Cu2 wt %, where Cu1 and Cu2 can be, independently, 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as Cu1<Cu2. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water. The concentration of water in the oxidation reaction product mixture exiting the oxidation reactor may range from C1a ppm to C1b ppm, based on the total weight of the oxidation reaction product mixture, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture portion, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently, 40, 45, 50, 55, 60, 65, 70, 75, 80, 85, 90, as long as Cc1<Cc2; and Cd1 and Cd2 can be, independently, 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently, 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently, 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

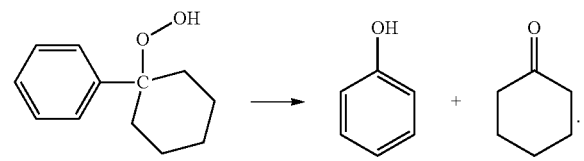
(Reaction-4)

The cleavage product mixture may comprise the acid catalyst, phenol, cyclohexanone cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction preferably occurs under cleavage conditions including a temperature in a range from 20° C. to 200° C., or from 40° C. to 120° C., and a pressure in a range from 1 to 370 psig (at least 7 kPa, gauge and no greater than 2,550 kPa, gauge), or from 14.5 psig to 145 psig (from 100 kPa, gauge to 1,000 kPa, gauge) such that the cleavage reaction mixture is completely or predominantly in the liquid phase during the cleavage reaction.

The cleavage reaction mixture can contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Preferably, Cac1 is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least AA wt %, where AA can be 90.0, 91.0, 92.0, 93.0, 94.0, 95.0, 96.0, 97.0, 98.0, 99.0, 99.5, 99.9, or even 100, the percentage based on the weight of a given hydroperoxide, or of all hydroperoxides fed to the cleavage step. This is desirable because any hydroperoxide, even the cyclohexyl-1-phenyl-1-hydroperoxide, becomes a contaminant in the downstream processes.

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation reaction product mixture, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently, 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; and (iii) cyclohexylbenzene at a concentration from Cchb7 wt % to Cchb8 wt %, where Cchb7 and Cchb8 can be, independently, 5, 8, 9, 10, 12, 14, 15, 18, 20, 22, 24, 25, 26, 28, 30, 35, 40, 45, 50, 55, 60, 65, 70, as long as Cchb7<Cchb8.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

Separation and Purification

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

Description According to the Drawing

Referring to FIG. 1, in a cyclohexylbenzene production system 101, a first distillation column 103 for the purpose of benzene feed preparation receives a benzene makeup (fresh benzene) from source 105 and a recycle benzene stream from source 107, and produces a first upper effluent 108 comprising water, benzene, hydrogen and lower aliphatics, which is cooled by heat exchanger 113, and then partly disposed of a light component stream 108b delivered to station 115, and partly recycled as a reflux stream 108b into the first distillation column 103. A reboiler 109 heats a recycle stream taken in the vicinity of the bottom of column 103 and thereby provides the required heat. Column 103 can be advantageously operated at an internal pressure close to atmospheric, a bottom temperature in the range from 85° C. to 100° C., and a top temperature in the range from 80° C. to 90° C., as long as the bottom temperature is higher than the top temperature.

A first middle effluent 110, consisting essentially of pure benzene, is withdrawn at a location relatively close to the top of the first distillation column 103, and fed into a first hydroalkylation reactor 117 together with a stream of hydrogen. Heat exchanger 121 heats the benzene and hydrogen feed 114 to the desired temperature in the range from 100° C. to 150° C., which travels downward in both liquid and vapor phase through a fixed bed of hydroalkylation catalyst comprising a precious metal (such as Ru, Rh, Pd, Re, Os, Ir, Pt) supported on a composite of an inorganic oxide (such as $Al_2O_3$, $SiO_2$, $ZrO_2$, $TiO_2$, $GeO_2$) binder and MCM-49 molecular sieve. Due to the exotherm of the hydroalkylation reaction, the first hydroalkylation effluent 116 exiting the bottom of the first hydroalkylation reactor 117 has a higher temperature than feed 114 in the range from 130° C. to 190° C., depending on the actual temperature of feed 114 and flow rate. A heat exchanger 123 cools down the first hydroalkylation effluent 116 to form a feed 118 having a temperature in the range from 100° C. to 150° C., which enters a second hydroalkylation reactor 119, passes downward through a second fixed bed of hydroalkylation catalyst therein, and exits the bottom of the second hydroalkylation reactor 119 as a second hydroalkylation effluent 120 having a temperature in the range from 130° C. to 190° C., depending on the actual temperature of feed 118 and flow rate. The first and second hydroalkylation reactors 117 and 119 operate at pressures ensuring that at least part of the benzene in the reaction medium is in liquid state. Alternatively (not shown), between the reactors 117 and 119, one or more similar hydroalkylation reactors may be situated, such that the whole hydroalkylation device comprising the multiple reactors achieves an overall desirable benzene conversion and cyclohexylbenzene conversion.

The second hydroalkylation effluent 120 is then fed into a separation drum 125, where the gas/liquid mixture is allowed to separate into a first lower drum effluent 124 consisting essentially of a liquid phase mixture comprising benzene, cyclohexane, cyclohexylbenzene, and the like, and a first upper drum effluent 122 consisting essentially of a gas phase mixture comprising hydrogen, benzene, cyclohexane, and the like. The liquid first lower drum effluent 124 is then supplied as part of the feed into a second distillation column 135, which produces a second lower effluent 132 comprising cyclohexylbenzene, C18 such as DiCHB, components comprising more than 18 carbons such as TriCHB, and the like, a second middle effluent 134 comprising benzene and cyclohexylbenzene, and a second upper effluent 140 comprising benzene having a higher benzene concentration compared to feed 130. Another upper effluent 142 comprising benzene at a higher benzene concentration compared to feed 130 is also produced and sent to a storage 136. Where needed, this benzene-rich liquid stored in 136 can be supplied back to the second distillation column 135. A reboiler 137 heats a recycle side stream taken in the vicinity of the bottom of column 135 and thereby provides heat thereto.

The second middle effluent 134 is fed into a third distillation column 139, which produces a third lower effluent 138 comprising high-purity cyclohexylbenzene in the vicinity of the bottom of the column. Part of effluent 138 is supplied as stream 138a to a storage station 143 for the subsequent cyclohexylbenzene oxidation step, and part of effluent 138 is heated by a reboiler 141 and recycled to the third distillation column 139. The third upper effluent 136 produced in the vicinity of the top of the third distillation column 139, which comprises benzene at a concentration higher than stream 134, is recycled to the second distillation column 135.

The first upper drum effluent 122, comprising hydrogen, cyclohexane and benzene, is heated by a furnace 145 and then fed into a dehydrogenation reactor 147 from the top thereof as feed stream 144. The radial-flow dehydrogenation reactor 147 comprises an annular bed of dehydrogenation catalyst 149 comprising a precious metal (such as Ru, Rh, Pd, Re, Os, Ir, Pt) supported on an inorganic oxide ($Al_2O_3$ and/or $SiO_2$) support. The reaction mixture travels inwardly in a substantially radial direction across the catalyst bed to the center space 151, whereby cyclohexane is partly converted into benzene and hydrogen, forms a dehydrogenation effluent 146 exiting the bottom of reactor 147. Effluent 146 heats the first drum upper effluent 122 via a heat exchanger 141 before effluent 122 is further heated by furnace 145. Subsequently, effluent 146 is further cooled by heat exchanger 153 to obtain a cooler gas mixture 148, which is compressed by a compressor 157 and delivered as stream 112b, which, together with a hydrogen makeup stream 112a from a hydrogen source 155, forms a combined stream 112, which, in turn, combines with the first middle effluent 110 from the benzene preparation distillation column 103, and forms feed stream 114 into the first hydroalkylation reactor 117. Alternatively (not shown), in addition to or in lieu of the makeup hydrogen stream 112a, a makeup hydrogen stream may be provided between two adjacent hydroalkylation reactors. Alternatively (not shown), the stream 148, comprising hydrogen, benzene and cyclohexane, is cooled and separated in a separation drum to obtain a liquid phase which is recycled to the first distillation column 103, and a gas phase which is compressed and sent to the first hydroalkylation reactor 117 as illustrated.

The second lower effluent 132 exiting the second distillation column 135, comprising C12 and C12+, is combined with a benzene-rich stream 140 taken in the vicinity of the top of column 135 and cooled by a heat exchanger 137 to form a transalkylation feed stream heated by a heat exchanger 133 before being fed into transalkylation reactor 131. Reactor 131 comprises a bed of transalkylation catalyst such as faujasite. The downflow of the transalkylation reaction medium in reactor 131 allows transalkylation reactions to occur on the surface of the catalyst, producing additional cyclohexylbenzene. The transalkylation effluent is then fed to a fourth distillation column 127, which produces (i) a fourth lower effluent comprising C18 and C18+ such as DiCHB, TriCHB, and the like, which is sent to purge station 129, and (ii) a fourth upper effluent 126 comprising cyclohexylbenzene and benzene, which is recycled to the second distillation column 135 as part of the feed thereto. A reboiler heats a recycle stream taken in the vicinity of the bottom of column 127 (which may be part of the fourth lower effluent).

The contents of all references cited herein are incorporated by reference in their entirety.

Thus, the present disclosure includes the following non-limiting aspects and/or embodiments:

I-1. A system for producing cyclohexylbenzene from benzene and hydrogen, the system comprising:

(I-1A) a first distillation column configured to receive a benzene feed and to produce a first bottom effluent comprising components having higher boiling points than benzene, a first middle effluent consisting essentially of benzene, and a first upper effluent comprising water, hydrogen and other components having lower boiling points than benzene;

(I-1B) a hydroalkylation device configured to produce a hydroalkylation production mixture comprising benzene, cyclohexane and cyclohexylbenzene, the device comprising a first hydroalkylation reactor, a second hydroalkylation reactor connected in series with the first hydroalkylation reactor and a first heat exchanger in between, wherein:

the first hydroalkylation reactor comprises a first hydroalkylation catalyst bed, is in fluid communication with the first distillation column, and is configured to receive (i) at least a portion of the first middle effluent and (ii) hydrogen at a location in the vicinity of the top thereof, to allow the reaction medium to travel downwards through the first hydroalkylation catalyst bed, and to produce a first hydroalkylation effluent at a location in the vicinity of the bottom thereof;

the first heat exchanger is configured to cool the first hydroalkylation effluent; and the second hydroalkylation reactor comprises a second hydroalkylation catalyst bed, is configured to receive, at a location in the vicinity of the top thereof, the cooled first hydroalkylation effluent supplied from the heat exchanger, allows the reaction medium to travel downwards through the second hydroalkylation catalyst bed, and produces a second hydroalkylation effluent at a location in the vicinity of the bottom thereof;

(I-1C) a first separation drum for separating the hydroalkylation production mixture into a first lower drum effluent comprising benzene, cyclohexane and cyclohexylbenzene, and a first upper drum effluent comprising hydrogen, benzene and cyclohexane;

(I-1D) a second distillation column in fluid communication with the first separation drum configured to receive at least a portion of the first lower drum effluent and to produce (i) a second lower effluent comprising C18 components at a location in the vicinity of the bottom of the second distillation column, (ii) a second middle effluent comprising benzene and cyclohexylbenzene, and (iii) a second upper effluent comprising benzene at a location in the vicinity of the top of the second distillation column;

(I-1E) a third distillation column in fluid communication with the second distillation column configured to receive at least a portion of the second middle effluent and to produce (i) a third lower effluent comprising at least 90 wt % of cyclohexylbenzene, the percentage based on the total weight of the third lower effluent, and (ii) a third upper effluent comprising benzene at a higher concentration than the second middle effluent, wherein at least a portion of the third upper effluent is recycled to the second distillation column at a location above the second middle effluent;

(I-1F) a transalkylation reactor comprising a transalkylation catalyst bed configured to receive at least a portion of the second lower effluent and benzene, to allow the transalkylation reaction medium travel downwards, and to produce a transalkylation effluent comprising cyclohexylbenzene, benzene and C18;

(I-1G) a fourth distillation column in fluid communication with the transalkylation reactor configured to receive at least a portion of the transalkylation effluent and to produce a fourth lower effluent comprising C18 and a fourth upper effluent comprising at least 50 wt % of benzene and cyclohexylbenzene, the percentage based on the total weight of the fourth upper effluent, wherein the fourth distillation column is in further fluid communication through which at least a portion of the fourth upper effluent is supplied to the second distillation column;

(I-1H) a dehydrogenation reactor comprising a bed of dehydrogenation catalyst in fluid communication with the first separation drum configured to receive at least a portion of the first upper drum effluent and to produce a dehydrogenation effluent comprising benzene, cyclohexane and hydrogen; and (I-1I) a recycle gas compressor in fluid communication with the dehydrogenation reactor and the first hydroalkylation reactor configured to deliver at least a portion of the hydrogen in the dehydrogenation effluent to the first hydroalkylation reactor.

I-2. The system of I-1, wherein the benzene feed received by the first distillation column comprises makeup benzene and recycled benzene, and the recycled benzene is derived from at least one of (i) an effluent drawn from the second distillation column in the vicinity of the top thereof; and (ii) at least a portion of the dehydrogenation effluent.

I-3. The system of I-1 or I-2, wherein:

the first distillation column is configured to operate at a temperature Tbzmax in the vicinity of the bottom thereof, and a temperature Tbzmin in the vicinity of the top thereof;

a1° C.≤Tbzmax≤a2° C., where a1 and a2 are, independently, 85, 86, 87, 88, 89, 90, 91, 92, 93, 94, 95, 96, 97, 98, 99, 100, 101, 102, 103, 104, and 105, as long as a1<a2;

b1 80° C.≤Tbzmin≤b2 90° C., where b1 and b2 are, independently, 80, 81, 82, 83, 84, 85, 86, 87, 88, 89, 90; as long as b1<b2; and Tbzmin<Tbzmax.

I-4. The system of any of I-1 to I-3, wherein:

the first hydroalkylation reactor is configured to operate at a temperature of T1hrmin in the vicinity of the top thereof, and a temperature of T1hrmax in the vicinity of the bottom thereof;

c1° C.≤T1hrmin≤c2° C., where c1 and c2 are, independently, 100, 105, 110, 115, 120, 125, 130, 135, 140, 145, 150, 155, and 160, as long as c1<c2; and d1° C.≤T1hrmax≤d2° C., where d1 and d2 are, independently, 130, 135, 140, 145, 150, 155, 160, 165, 170, 175, 180, 185, 190, 195, 200, as long as d1<d2; and T1hrmin<T1hrmax.

I-5. The system of any of I-1 to I-4, wherein:

the second hydroalkylation reactor has an upper temperature of T2hrmin in the vicinity of the top thereof, a temperature of T2hrmax in the vicinity of the bottom thereof;

e1° C.≤T2hrmin≤e2° C., where e1 and e2 are, independently, 100, 105, 110, 115, 120, 125, 130, 135, 140, 145, 150, 155, and 160, as long as e1<e2; and f1° C.≤T2hrmax≤f2° C., where f1 and f2 are, independently, 130, 135, 140, 145, 150, 155, 160, 165, 170, 175, 180, 185, 190, 195, 200, as long as f1<f2; and T2hrmin<T2hrmax.

I-6. The system of I-5, wherein g1° C.≤|T1hrmax−T2hrmin|≤g2° C., where g1 and g2 are, independently, 15, 18, 20, 23, 25, 28, 30, 33, 35, 38, 40, 43, 45, 48, 50, as long as g1<g2.

I-7. The system of I-5 or I-6, wherein 15≤|T1hrmax−T2hrmax|≤20° C.

I-8. The system of any of I-5 to I-7, where T1hrmax>T2hrmax.

I-9. The system of any of the preceding claims, wherein at least one of the first distillation column, the second distillation column, the third distillation column and the fourth distillation column is configured to operate at an internal absolute pressure of at least 100 kPa.

I-10. The system of I-9, wherein all of the first distillation column, the second distillation column, the third distillation column and the fourth distillation column is configured to operate at an internal absolute pressure of at least 100 kPa.

I-11. The system of I-9 or I-10, wherein at least one, preferably all, of the first distillation column, the second distillation column, the third distillation column and the fourth distillation column is configured to operate at an internal absolute pressure from P1 kPa to P2 kPa, where P1 and P2 are, independently, 101, 105, 110, 120, 130, 140, 150, 160, 180, 200, 250, 300, 350, 400, 450, 500, 550, 600, 650, 700, 750, 800, 850, 900, 950, 1000, as long as P1<P2.

I-12. The system of any of I-1 to I-11, wherein each of the first distillation column, the second distillation column, the third distillation column, and the fourth distillation column comprises a reboiler providing heat to the fluid inside the column.

I-13. The system of I-2, wherein a portion of the recycled benzene is derived from the second upper effluent.

I-14. The system of I-2, wherein a portion of the recycled benzene is derived from an effluent drawn from the second distillation column in the vicinity of the top thereof below the second upper effluent and above the second middle effluent.

I-15. The system of any of I-1 to I-14, wherein at least a portion of the benzene received by the transalkylation reactor is derived from the second upper effluent.

I-16. The system of any of I-1 to I-15, wherein the feeds received by the transalkylation reactor comprises a mixture of at least a portion of the second lower effluent and a portion of the second upper effluent, the mixture having been cooled down by a heat exchanger before entering the transalkylation reactor.

I-17. The system of any of I-1 to I-16, wherein at least one of the following is supplied to a combustor and combusted to provide heat to at least one of the components in the system:

(17.1) at least a portion of the first upper effluent;

(17.2) at least a portion of the first lower effluent; and (17.3) at least a portion of the fourth lower effluent.

I-18. The system of any of I-1 to I-17, wherein the dehydrogenation catalyst comprises an inorganic oxide support and at least one metal selected from Group 9 and Group 10 of the Periodic Table of Elements.

I-19. The system of I-18, wherein the metal is selected from Ru, Rh, Pd, Os, Ir, Pt, and combinations thereof.

I-20. The system of I-18 or I-19, wherein the inorganic oxide support comprises at least one of $SiO_2$, $Al_2O_3$, $TiO_2$, and $ZrO_2$.

I-21. The system of any of I-1 to I-20, wherein the dehydrogenation reactor comprises a radial flow reactor comprising an annulus bed of dehydrogenation catalyst.

I-22. The system of I-21, wherein the annulus bed has a radial thickness Thcat, wherein T1 cm≤Thcat≤T2 cm, where T1 and T2 are, independently, 2.5, 3.0, 4.0, 5.0, 7.5, 10, 15, 20, 25, 30, 35, 40, 45, 50, as long as T1<T2.

I-23. The system of I-21 or I-22, wherein the dehydrogenation reactor is configured to receive the feed at a location in the vicinity of the top thereof, and to produce the dehydrogenation effluent at a location in the vicinity of the bottom thereof.

I-24. The system of any of I-21 to I-23, wherein the dehydrogenation reactor is configured to receive the feed supplied to the outer annulus between the reactor wall and the bed of the dehydrogenation catalyst, and to allow the reaction medium to flow inwardly in a radial direction.

I-25. The system of any of the preceding claims, wherein at least a portion of the first upper drum effluent is heated by the dehydrogenation effluent via a heat exchanger before being fed into the dehydrogenation reactor.

I-26. The system of I-25, wherein the at least a portion of the first upper drum effluent is further heated by a furnace before being fed into the dehydrogenation reactor.

I-27. The system of any of I-1 to I-26, further comprising:
(I-1J) a second separation drum in fluid communication with the dehydrogenation reactor configured to receive the dehydrogenation effluent and to produce a second gas upper drum effluent comprising hydrogen, and a second liquid lower drum effluent comprising benzene, the second separation drum is in further fluid communication with the recycle gas compressor through which at least a portion of the hydrogen in the second upper drum effluent is recycled to the hydroalkylation device.

I-28. The system of I-27, wherein the second separation drum is in further fluid communication with the first distillation column through which at least a portion of the second liquid lower drum effluent is recycled to the first distillation column as part of the benzene feed.

II-1. A process for making cyclohexylbenzene from benzene and hydrogen using a system according to any of I-1 to I-28.

The invention claimed is:

1. A system for producing cyclohexylbenzene from benzene and hydrogen, the system comprising:
(A) a first distillation column configured to receive a benzene feed and to produce a first bottom effluent comprising components having higher boiling points than benzene, a first middle effluent consisting essentially of benzene, and a first upper effluent comprising water, hydrogen and other components having lower boiling points than benzene;
(B) a hydroalkylation device configured to produce a hydroalkylation production mixture comprising benzene, cyclohexane and cyclohexylbenzene, the device comprising a first hydroalkylation reactor, a second hydroalkylation reactor connected in series with the first hydroalkylation reactor and a first heat exchanger in between, wherein:
the first hydroalkylation reactor comprises a first hydroalkylation catalyst bed, is in fluid communication with the first distillation column, and is configured to receive (i) at least a portion of the first middle effluent and (ii) hydrogen at a location in the vicinity of the top thereof, to allow the reaction medium to travel downwards through the first hydroalkylation catalyst bed, and to produce a first hydroalkylation effluent at a location in the vicinity of the bottom thereof;
the first heat exchanger is configured to cool the first hydroalkylation effluent; and
the second hydroalkylation reactor comprises a second hydroalkylation catalyst bed, is configured to receive, at a location in the vicinity of the top thereof, the cooled first hydroalkylation effluent supplied from the heat exchanger, allows the reaction medium to travel downwards through the second hydroalkylation catalyst bed, and produces a second hydroalkylation effluent at a location in the vicinity of the bottom thereof;
(C) a first separation drum for separating the hydroalkylation production mixture into a first lower drum effluent comprising benzene, cyclohexane and cyclohexylbenzene, and a first upper drum effluent comprising hydrogen, benzene and cyclohexane;
(D) a second distillation column in fluid communication with the first separation drum configured to receive at least a portion of the first lower drum effluent and to produce (i) a second lower effluent comprising C18 components at a location in the vicinity of the bottom of the second distillation column, (ii) a second middle effluent comprising benzene and cyclohexylbenzene, and (iii) a second upper effluent comprising benzene at a location in the vicinity of the top of the second distillation column;
(E) a third distillation column in fluid communication with the second distillation column configured to receive at least a portion of the second middle effluent and to produce (i) a third lower effluent comprising at least 90 wt % of cyclohexylbenzene, the percentage based on the total weight of the third lower effluent, and (ii) a third upper effluent comprising benzene at a higher concentration than the second middle effluent, wherein at least a portion of the third upper effluent is recycled to the second distillation column at a location above the second middle effluent;
(F) a transalkylation reactor comprising a transalkylation catalyst bed configured to receive at least a portion of the second lower effluent and benzene so as to form a transalkylation reaction medium which travels downwards through the transalkylation reactor, and to produce a transalkylation effluent comprising cyclohexylbenzene, benzene and C18;
(G) a fourth distillation column in fluid communication with the transalkylation reactor configured to receive at least a portion of the transalkylation effluent and to produce a fourth lower effluent comprising C18 and a fourth upper effluent comprising at least 50 wt % of benzene and cyclohexylbenzene, the percentage based on the total weight of the fourth upper effluent, wherein the fourth distillation column is in further fluid communication through which at least a portion of the fourth upper effluent is supplied to the second distillation column;
(H) a dehydrogenation reactor comprising a bed of dehydrogenation catalyst in fluid communication with the first separation drum configured to receive at least a portion of the first upper drum effluent and to produce a dehydrogenation effluent comprising benzene, cyclohexane and hydrogen; and
(I) a recycle gas compressor in fluid communication with the dehydrogenation reactor and the first hydroalkylation reactor configured to deliver at least a portion of the hydrogen in the dehydrogenation effluent to the first hydroalkylation reactor.

2. The system of claim 1, wherein the benzene feed received by the first distillation column comprises makeup benzene and recycled benzene, and the recycled benzene is derived from at least one of (i) an effluent drawn from the second distillation column in the vicinity of the top thereof; and (ii) at least a portion of the dehydrogenation effluent.

3. The system of claim 2, wherein a portion of the recycled benzene is derived from the second upper effluent.

4. The system of claim 3, wherein a portion of the recycled benzene is derived from an effluent drawn from the second distillation column in the vicinity of the top thereof below the second upper effluent and above the second middle effluent.

5. The system of claim 1, wherein the first distillation column is configured to operate at a temperature Tbzmax in the vicinity of the bottom thereof, and a temperature Tbzmin in the vicinity of the top thereof, 85° C.≤Tbzmax≤105° C., and 80° C.≤Tbzmin≤90° C., as long as Tbzmin<Tbzmax.

6. The system of claim 1, wherein the first hydroalkylation reactor is configured to operate at a temperature of T1hrmin in the vicinity of the top thereof, a temperature of T1hrmax in the vicinity of the bottom thereof, 100° C.≤T1hrmin≤160° C., and 130° C.≤T1hrmax≤200° C., as long as T1hrmin<T1hrmax.

7. The system of claim 1, wherein the second hydroalkylation reactor has an upper temperature of T2hrmin in the vicinity of the top thereof, a temperature of T2hrmax in the vicinity of the bottom thereof, 100° C.≤T2hrmin≤160° C., and 130≤T2hrmax≤200° C., as long as T2hrmin<T2hrmax.

8. The system of claim 7, wherein 15° C.≤|T1hrmax−T2hrmin|≤50° C.

9. The system of claim 7, wherein |T1hrmax−T2hrmax|≤20° C.

10. The system of claim 1, wherein at least one of the first distillation column, the second distillation column, the third distillation column and the fourth distillation column is configured to operate at an internal absolute pressure of at least 100 kPa.

11. The system of claim 10, wherein all of the first distillation column, the second distillation column, the third distillation column and the fourth distillation column are configured to operate at internal absolute pressures higher than 100 kPa.

12. The system of claim 1, wherein each of the first distillation column, the second distillation column, the third distillation column, and the fourth distillation column comprises a reboiler providing heat to the fluid inside the column.

13. The system of claim 1, wherein at least a portion of the benzene received by the transalkylation reactor is derived from the second upper effluent.

14. The system of claim 1, wherein the feeds received by the transalkylation reactor comprises a mixture of at least a portion of the second lower effluent and a portion of the second upper effluent, the mixture having been cooled down by a heat exchanger before entering the transalkylation reactor.

15. The system of claim 1, wherein at least one of the following is supplied to a combustor and combusted to provide heat to at least one of the components in the system:
   (1) at least a portion of the first upper effluent;
   (2) at least a portion of the first lower effluent; and
   (3) at least a portion of the fourth lower effluent.

16. The system of claim 1, wherein the dehydrogenation catalyst comprises an inorganic oxide support and a metal selected from Ru, Rh, Pd, Os, Ir, Pt, and combinations thereof.

17. The system of claim 1, wherein the dehydrogenation reactor comprises a radial flow reactor comprising an annulus bed of dehydrogenation catalyst.

18. The system of claim 17, wherein the annulus bed has a radial thickness Thcat, wherein 2.5 cm≤Thcat≤50 cm.

19. The system of claim 17, wherein the dehydrogenation reactor is configured to receive the feed at a location in the vicinity of the top thereof, and to produce the dehydrogenation effluent at a location in the vicinity of the bottom thereof.

20. The system of claim 17, wherein the dehydrogenation reactor is configured to receive the feed supplied to the outer annulus between the reactor wall and the bed of the dehydrogenation catalyst, and to allow the reaction medium to flow inwardly in a radial direction.

21. The system of claim 1, wherein at least a portion of the first upper drum effluent is heated by the dehydrogenation effluent via a heat exchanger before being fed into the dehydrogenation reactor.

22. The system of claim 21, wherein the at least a portion of the first upper drum effluent is further heated by a furnace before being fed into the dehydrogenation reactor.

23. The system of claim 1, further comprising:
   (J) a second separation drum in fluid communication with the dehydrogenation reactor configured to receive the dehydrogenation effluent and to produce a second gas upper drum effluent comprising hydrogen, and a second liquid lower drum effluent comprising benzene, the second separation drum is in further fluid communication with the recycle gas compressor through which at least a portion of the hydrogen in the second upper drum effluent is recycled to the hydroalkylation device.

24. The system of claim 23, wherein the second separation drum is in further fluid communication with the first distillation column through which at least a portion of the second liquid lower drum effluent is recycled to the first distillation column as part of the benzene feed.

* * * * *